(12) United States Patent
Strickland

(10) Patent No.: US 8,273,098 B2
(45) Date of Patent: Sep. 25, 2012

(54) CARPAL TUNNEL RELEASE TOOL

(75) Inventor: James W. Strickland, Indianapolis, IN (US)

(73) Assignee: Del Palma Orthopedics, LLC, Columbia City, IN (US)

( * ) Notice: Subject to any disclaimer, the term of this patent is extended or adjusted under 35 U.S.C. 154(b) by 64 days.

(21) Appl. No.: 12/836,648

(22) Filed: Jul. 15, 2010

(65) Prior Publication Data

US 2012/0016398 A1    Jan. 19, 2012

(51) Int. Cl.
 *A61B 17/32* (2006.01)
(52) U.S. Cl. ......................................... 606/170; 606/191
(58) Field of Classification Search .................. 606/167, 606/170, 138, 148, 150, 166, 190, 191; 600/183; 30/289, 294

See application file for complete search history.

(56) References Cited

U.S. PATENT DOCUMENTS

| | | | | | |
|---|---|---|---|---|---|
| 3,678,581 | A | * | 7/1972 | Bolduc | 30/294 |
| 3,975,822 | A | * | 8/1976 | Mabus | 30/294 |
| 5,273,024 | A | * | 12/1993 | Menon et al. | 600/114 |
| 5,282,816 | A | * | 2/1994 | Miller et al. | 606/167 |
| 5,569,283 | A | * | 10/1996 | Green et al. | 606/170 |
| 6,019,774 | A | * | 2/2000 | Weiss et al. | 606/167 |
| 2004/0054378 | A1 | * | 3/2004 | Yang | 606/191 |
| 2004/0098005 | A1 | * | 5/2004 | Mirza et al. | 606/170 |
| 2008/0255600 | A1 | * | 10/2008 | Braam et al. | 606/190 |
| 2009/0048620 | A1 | * | 2/2009 | Weiss et al. | 606/167 |
| 2011/0252651 | A1 | * | 10/2011 | Sewell | 30/289 |

* cited by examiner

*Primary Examiner* — Ryan Severson
*Assistant Examiner* — David Eastwood
(74) *Attorney, Agent, or Firm* — Heslin Rothenberg Farley & Mesiti P.C.

(57) ABSTRACT

A carpal tunnel release tool and methods for using the same are disclosed. Embodiments of the carpal tunnel release tool include a guide with an angled track and a knife that fits into and follows the angled track. In one embodiment, the knife is retracted into the guide as it is advanced along the track to cut the ligament. In an alternate embodiment the blade is extended outwardly from the surface of the guide as the blade is advanced along the track. Other embodiments include a projection at the terminal end of the track that maintains the position of the ligament over the guide, serves as a type of cutting block to ensure complete bisecting of the ligament, and can aid the surgeon in placement of the guide beneath the ligament. Further embodiments include an inserter that inhibits tissue entering the track as the guide is advanced beneath the ligament.

15 Claims, 20 Drawing Sheets

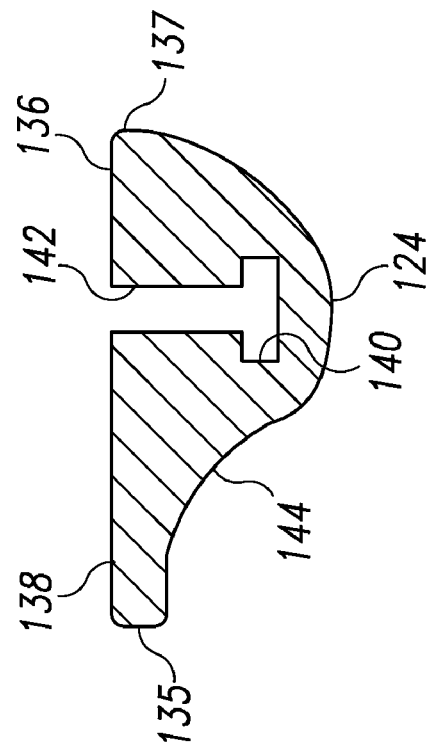
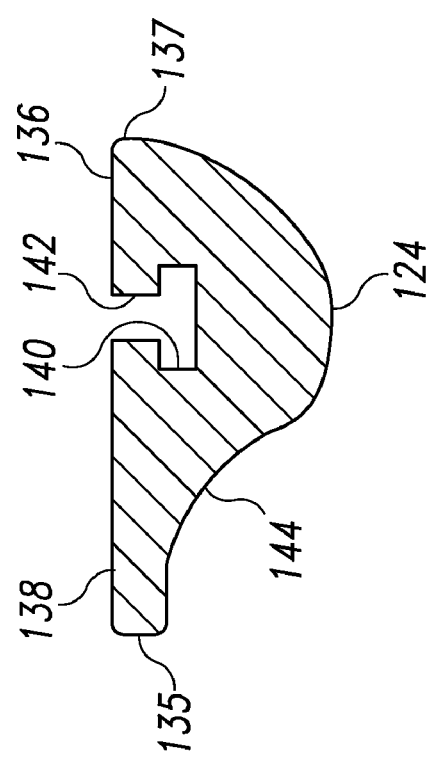

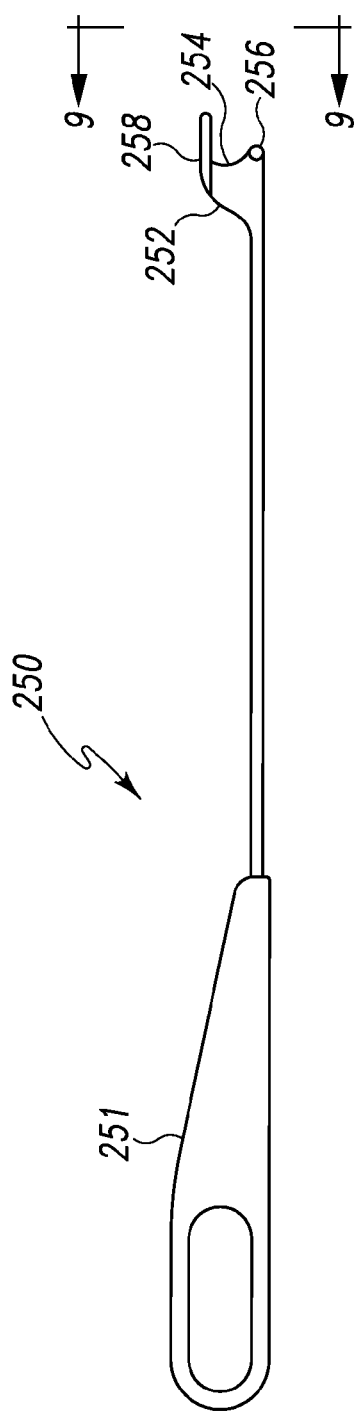
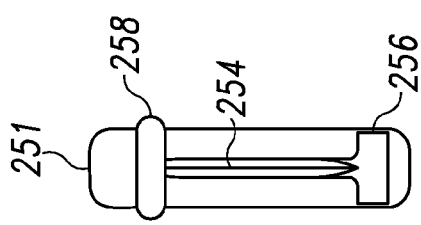
Fig. 8
Fig. 9

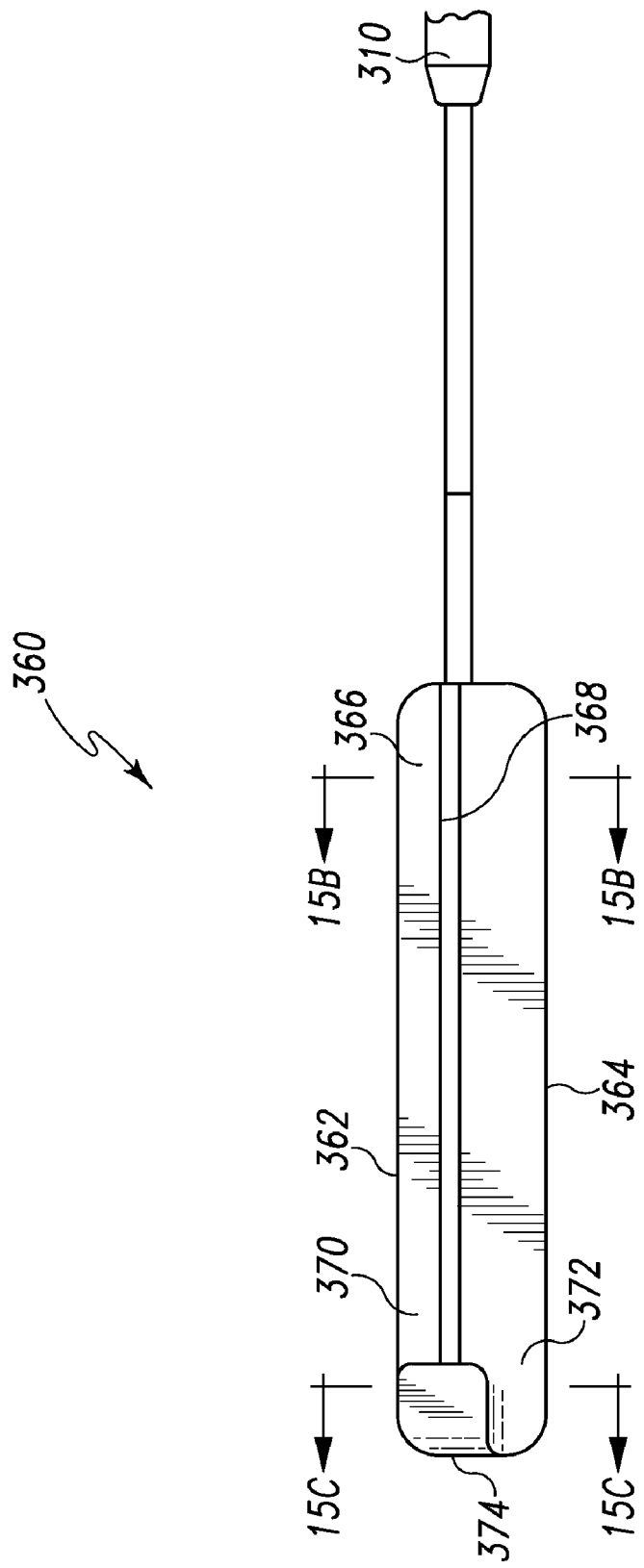

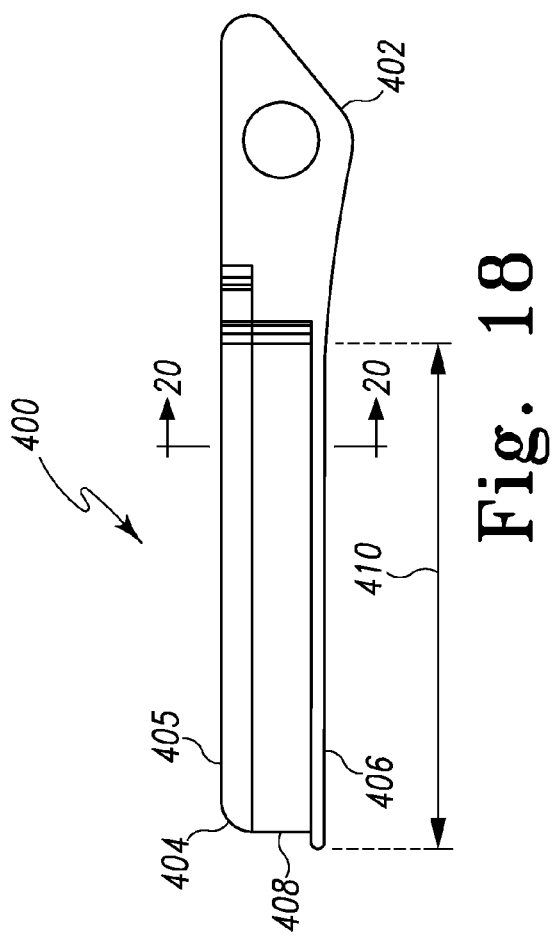
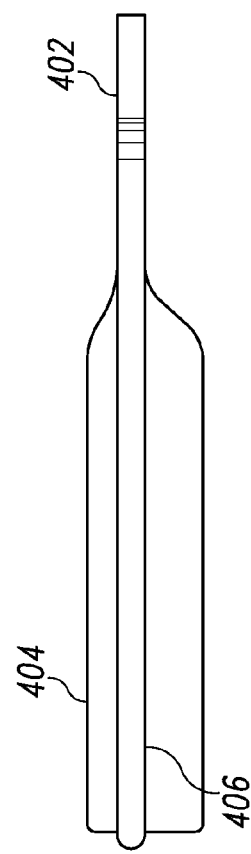
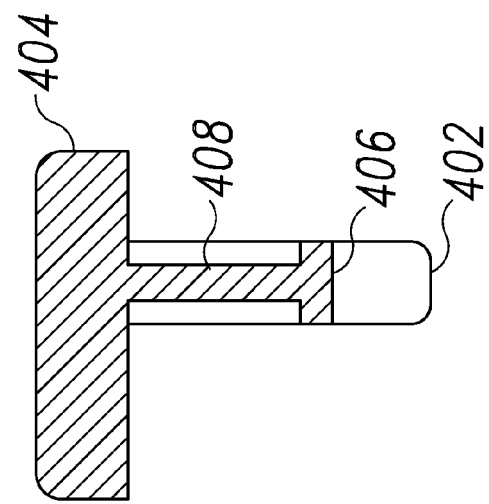

CARPAL TUNNEL RELEASE TOOL

BACKGROUND

The carpal tunnel is a space in the palm region of a human hand. The floor of the carpal tunnel is formed by a concave arch of carpal bones that are covered by wrist ligaments. The roof of the carpal tunnel is formed by the transverse carpal ligament extending in the transverse direction across the wrist from the base of the thumb to the outer portion of the wrist bones. The carpal tunnel forms a conduit for the median nerve (which innervates portions of the index, middle and ring fingers, and the thumb) and nine digital flexor tendons (which control finger movement) extending from the forearm into the palm.

Carpal tunnel syndrome is a condition where the median nerve is compressed within the carpal tunnel, resulting in pain and/or numbness in the wrist and/or hand. Compression of the median nerve can result from a reduction in the size of the carpal tunnel, an increase in the volume of the tissue inside the carpal tunnel, or by movement of the flexor tendons. Compression of the median nerve can cause pain, numbness or a prickly, tingling sensation in the wrist, hand, fingers or thumb that can radiate to the forearm.

A surgical technique for relieving pressure within the carpal tunnel includes bisecting the transverse carpal ligament that forms the roof of a carpal tunnel. Once the transverse carpal ligament is cut, the pressure within the carpal tunnel is relieved and the pain, numbness and/or tingling caused by compression of the median nerve is reduced or eliminated.

The transverse carpal ligament is generally cut in a direction transverse to the ligament, which is approximately along a line drawn from the patient's elbow to the patient's fingers. Along the direction of the cut, the thickness of the transverse carpal ligament is not constant. The transverse carpal ligament is thinnest on the proximal side (side nearest the elbow) and thickest on the distal side (side nearest the fingers). Schematic diagrams of the transverse carpal ligament and the carpal tunnel are illustrated in prior U.S. patents, such as U.S. Pat. Nos. 5,507,800 and 6,179,852, the disclosure of which is incorporated by reference.

In bisecting the transverse carpal ligament, a surgeon must take care to avoid damaging the median nerve and other vital tissue extending beneath the transverse carpal ligament. Damaging the median nerve can result in long-term pain or limited mobility. Although no nerves overlie the transverse carpal ligament, cutting the tissue above the transverse carpal ligament increases short-term pain and recovery time following an operation. Despite these disadvantages, surgeons cut the tissue overlying the transverse carpal ligament during carpal tunnel release surgery.

It was realized by the inventor of the current invention that improvements in tools for bisecting the transverse carpal ligament are needed. For example, it was realized that improvements in guides for bisecting the transverse carpal ligament that avoid damage to the median nerve and minimize damage to the tissue overlying the transverse carpal ligament are needed.

Certain preferred features of the present invention address these and other needs and provide other important advantages. Some or all of these features may be present in the corresponding independent or dependent claims, but should not be construed to be a limitation unless expressly recited in a particular claim.

SUMMARY

Embodiments of the present invention provide an improved carpal tunnel release tool. In accordance with a first aspect of embodiments of the present invention, a carpal tunnel release tool with a guide and a knife is provided. The guide includes an angled track into which the knife fits. The knife is restricted to move along the track. As the knife is moved along the track, the knife is retracted into the guide.

In accordance with another aspect of embodiments of the present invention, a carpal tunnel release tool with a guide and a knife is provided. The guide includes an angled track into which the knife fits. The knife is restricted to move along the track. As the knife is advanced along the track, the knife extends out from the surface of the guide.

In accordance with yet another aspect of embodiments of the present invention, a carpal tunnel release tool with a guide and a knife is provided. The guide includes an angled track into which the knife fits and the knife is restricted to move along the track. The guide further includes a raised portion which allows the surgeon to determine when the guide sufficiently underlies the transverse carpal ligament to begin the cutting procedure.

In accordance with a further aspect of embodiments of the present invention, a carpal tunnel release tool includes a guide and a knife. The guide further includes a raised receptacle for the knife at the end of the track where the raised receptacle serves as a housing for the knife that encloses at least the cutting edge of the extended knife and further serves as an abutment to prevent the transverse carpal ligament from sliding off of the guide as it is being cut by the knife.

This summary is provided to introduce a selection of the concepts that are described in further detail in the detailed description and drawings contained herein. This summary is not intended to identify any primary or essential features of the claimed subject matter, nor is it intended to be used as an aid in determining the scope of the appended claims. Each embodiment described herein is not intended to address every object described herein, and each embodiment does not include each feature described. Other forms, embodiments, objects, advantages, benefits, features, and aspects of the present invention will become apparent to one of skill in the art from the detailed description and drawings contained herein.

BRIEF DESCRIPTION OF THE DRAWINGS

FIG. 4A is a cross-sectional view of the guide depicted in FIG. 2 taken along line 4A-4A.

FIG. 4B is a cross-sectional view of the guide depicted in FIG. 2 taken along line 4B-4B.

FIG. 8 is a side elevational view of a knife according to another embodiment of the present invention.

FIG. 9 is a front elevational view of the knife depicted in FIG. 8 taken from the perspective of line 9-9.

FIG. 15A is fragmentary, a top plan view of a guide according to another embodiment of the present invention.

FIG. 18 is a side elevational view of an inserter according to one embodiment of the present invention.

FIG. 19 is a top plan view of the inserter depicted in FIG. 18.

FIG. 20 is a cross-sectional view of the inserter depicted in FIG. 18 taken along line 20-20.

DETAILED DESCRIPTION OF THE ILLUSTRATED EMBODIMENTS

Figure 1:
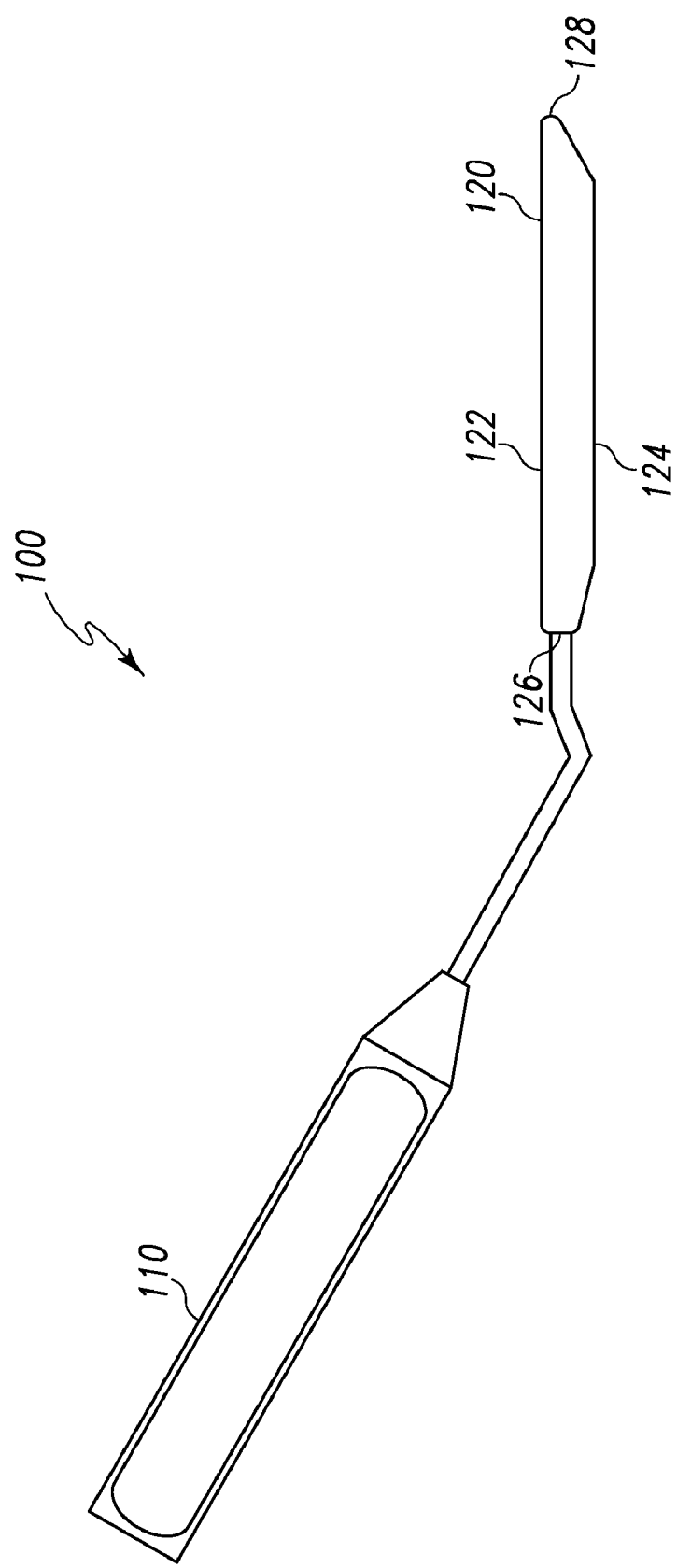
FIG. 1 is a side elevational view of a guide according to one embodiment of the present invention.

For the purposes of promoting an understanding of the principles of the invention, reference will now be made to the selected embodiments illustrated in the drawings and specific language will be used to describe the same. It will nevertheless be understood that no limitation of the scope of the invention is hereby intended, such alterations, modifications, and further applications of the principles of the invention being contemplated as would normally occur to one skilled in the art to which the invention relates. At least one embodiment of the invention is shown in great detail, although it will be apparent to those skilled in the relevant art that some features or some combinations of features may not be shown for the sake of clarity.

In accordance with one embodiment of the present invention, a carpal tunnel release tool that assists a surgeon in cutting the transverse carpal ligament without damaging the underlying nerves and tissue while minimizing damage to the tissue overlying the transverse carpal ligament is disclosed. The carpal tunnel release tool comprises a cutting guide and a cutting knife that slidingly engage along a T-shaped track in the cutting guide. When viewed along its length, the cross-sectional shape of the cutting knife is T-shaped and complimentary to a T-shaped channel extending along a substantial portion of the cutting guide. In alternate embodiments, the T-shaped channel angles downward or upward from the handle to the tip depending on how the ligament's thickness varies in the direction the cut is made. This angling of the T-shaped channel compensates for the variation in the transverse carpal ligament's thickness along a line extending from the fingers to the elbow. The transverse carpal ligament is thickest in the portion nearest the fingers, thinnest in the portion nearest the elbow, and tapers between these two portions.

Depicted in FIGS. 1, 2, 3, 4A and 4B is a distal-to-proximal carpal tunnel release guide 100 for surgery on the right hand according to one embodiment of the present invention. The distal-to-proximal guide 100 is for inserted through a cut in the skin distal to the transverse carpal ligament (near the side of the carpal tunnel ligament that is closest to the fingers). The guide 100 is then advanced toward to the proximal side of the transverse carpal ligament (the side of the transverse carpal ligament nearer to the elbow) before the cutting knife is inserted to bisect the transverse carpal tunnel ligament.

The distal-to-proximal carpal tunnel release guide 100 for surgery on the right hand includes a handle 110 and a guide portion 120. Guide portion 120 includes an upper surface 122, a lower surface 124, an opening end 126 and a terminal end 128. The upper surface 122 extends from the left side 135 to the right side 137 and from the guide opening end 126 to the guide terminal end. The left side 135 and the right side 137 are labeled to coincide with the left and right perspective of a surgeon holding guide 100 during surgery.

Guide portion 120 further includes a track 130, which includes a track opening 132 and a track terminal end 134. The path of track 130 follows the path of the upper surface of the transverse carpal ligament as it lies on top of guide upper surface 122. In the depicted embodiment, track 130 follows a constantly descending straight line, although in alternate embodiments the slope of track 130 varies between track opening 132 and track terminal end 134, with track 130 being curved in whole or in part along its length.

Figure 2:
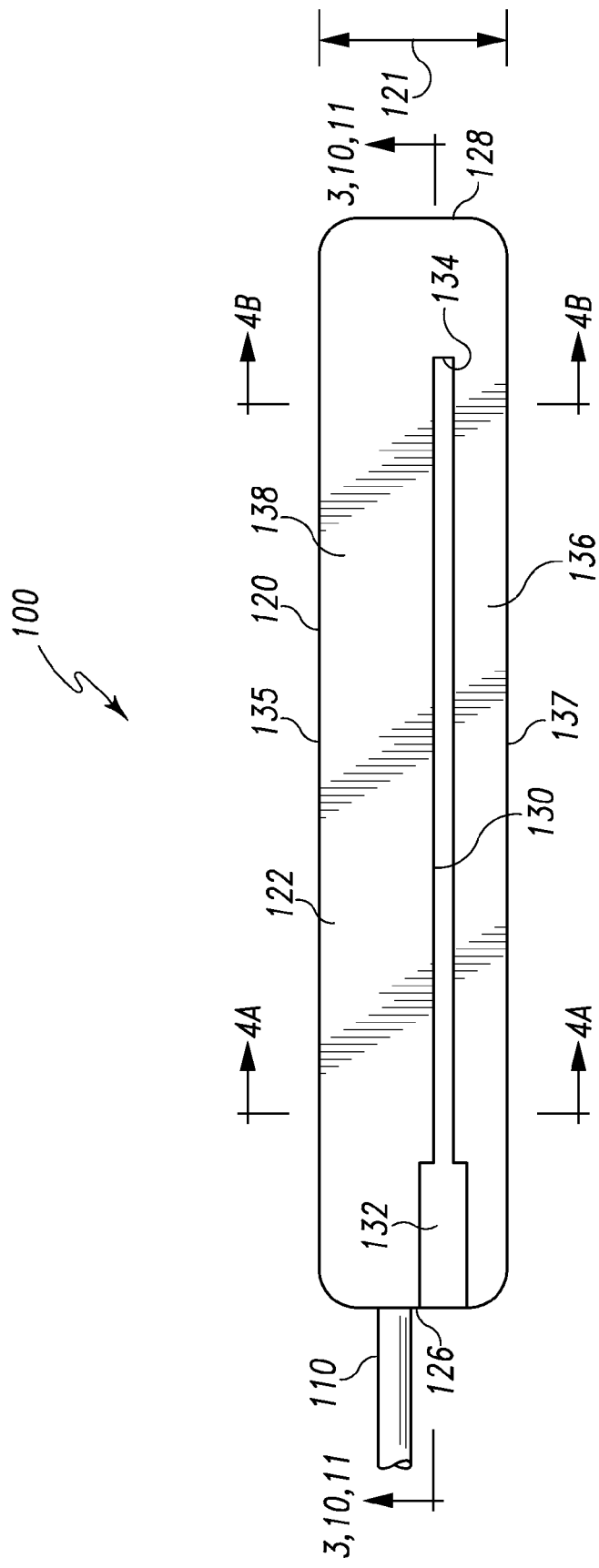
FIG. 2 is a fragmentary top plan view of the guide depicted in FIG. 1.

As best seen in the illustrated embodiment depicted in FIG. 2, track 130 is offset to one side of upper surface 122 forming a narrow side 136 of the upper surface 122 on the side of the upper surface 122 to which track 130 is displaced, and a widened side 138 of upper surface 122 on the side of upper surface 122 from which track 130 is displaced. The track 130 is positioned nearer to the left side 135 than to the right side 137. In the illustrated embodiment, the track 130 is positioned approximately one-third (⅓) the width 121 of guide 100 (the distance between right side 137 and left side 135) from the left side 135, and approximately two-thirds (⅔) the width of guide 100 from the right side 137. In the illustrated embodiment, the width 121 of guide 100 is approximately nine millimeters (9 mm). In other embodiments, the width 121 of guide 100 is at least five millimeters (5 mm) and at most thirty millimeters (30 mm). In still further embodiments, the width 121 of guide 100 is at least seven millimeters (7 mm) and at most thirteen millimeters (13 mm).

Figure 3:
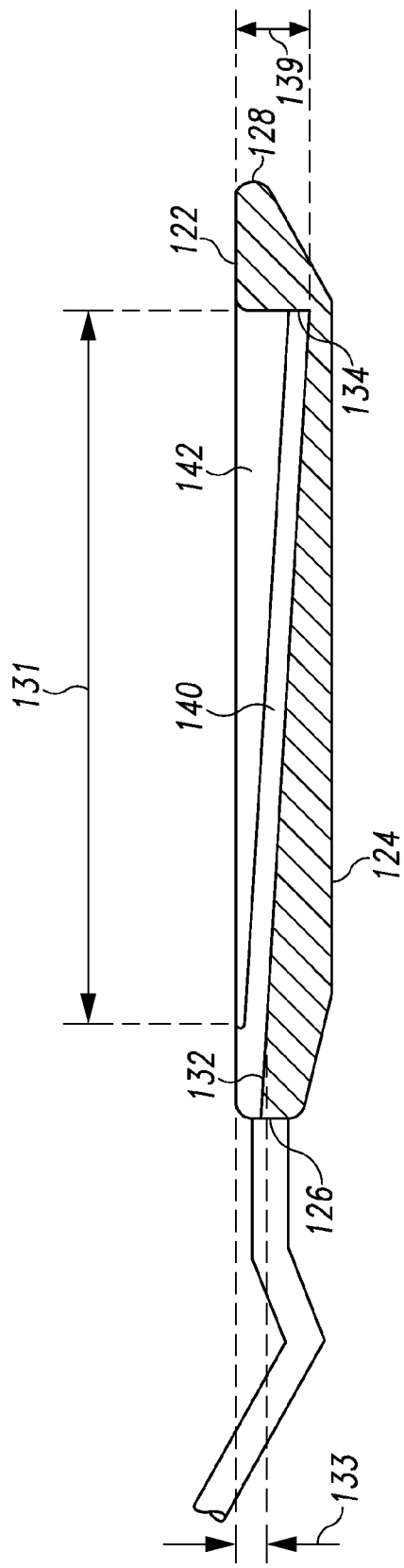
FIG. 3 is a fragmentary, cross-sectional view of the guide depicted in FIG. 2 taken along line 3-3.

Track 130 further includes a wide portion 140 and a narrow portion 142, as best seen in FIGS. 3, 4A and 4B. Track 130 angles downward from track opening 132 (adjacent guide opening end 126) to track terminal end 134 (adjacent guide terminal end 128).

The bottom surface 124 of guide 100 includes a concave portion 144, which is located beneath the widened side 138 of upper surface 122. When guide 100 is inserted under the transverse carpal ligament, the concave portion 144 accommodates the median nerve to minimize trauma during carpal tunnel release surgery.

In the illustrated embodiment, the length 131 of track 130 is approximately three centimeters (3.0 cm). In alternate embodiments the length 131 of track 130 is at least one centimeter (1.0 cm) and at most five centimeters (5.0 cm). In still further embodiments, the length 131 of track 130 is at least two centimeters (2.0 cm) and at most four centimeters (4.0 cm).

Along the length 131 of track 130, the depth of track 130 below the upper surface 122 of guide portion 120 increases from the opening 132 to the terminal end 134. In the illustrated embodiment, track depth 133 at track opening 132 is approximately four-fifths millimeters (0.8 mm) and the track depth 139 at track terminal end 134 is approximately three and one-half millimeters (3.5 mm). When using a cutting blade 220 that extends approximately four and one-half millimeters (4.5 mm) above the bottom of track 130, the upper end 222 (see FIGS. 6 and 7) of blade 220 extends approximately three and seven-tenths millimeters (3.7 mm) above upper surface 122 at track opening 132 and extends approximately one millimeter (1.0 mm) above upper surface 122 at the track terminal end 134. Since a typical transverse carpal ligament is approximately three millimeters (3.0 mm) thick at the distal edge (edge nearest the fingers), the cutting blade extends approximately seven-tenths millimeters (0.7 mm) above the top of the transverse carpal ligament. In alternate embodiments, the upper end 222 of blade 220 extends approximately four-tenths millimeters (0.4 mm) above the top of the transverse carpal ligament. In still further embodiments, the upper end 222 of blade 220 extends one-fifth millimeters (0.2 mm) above the top of the transverse carpal ligament.

Figure 5A:
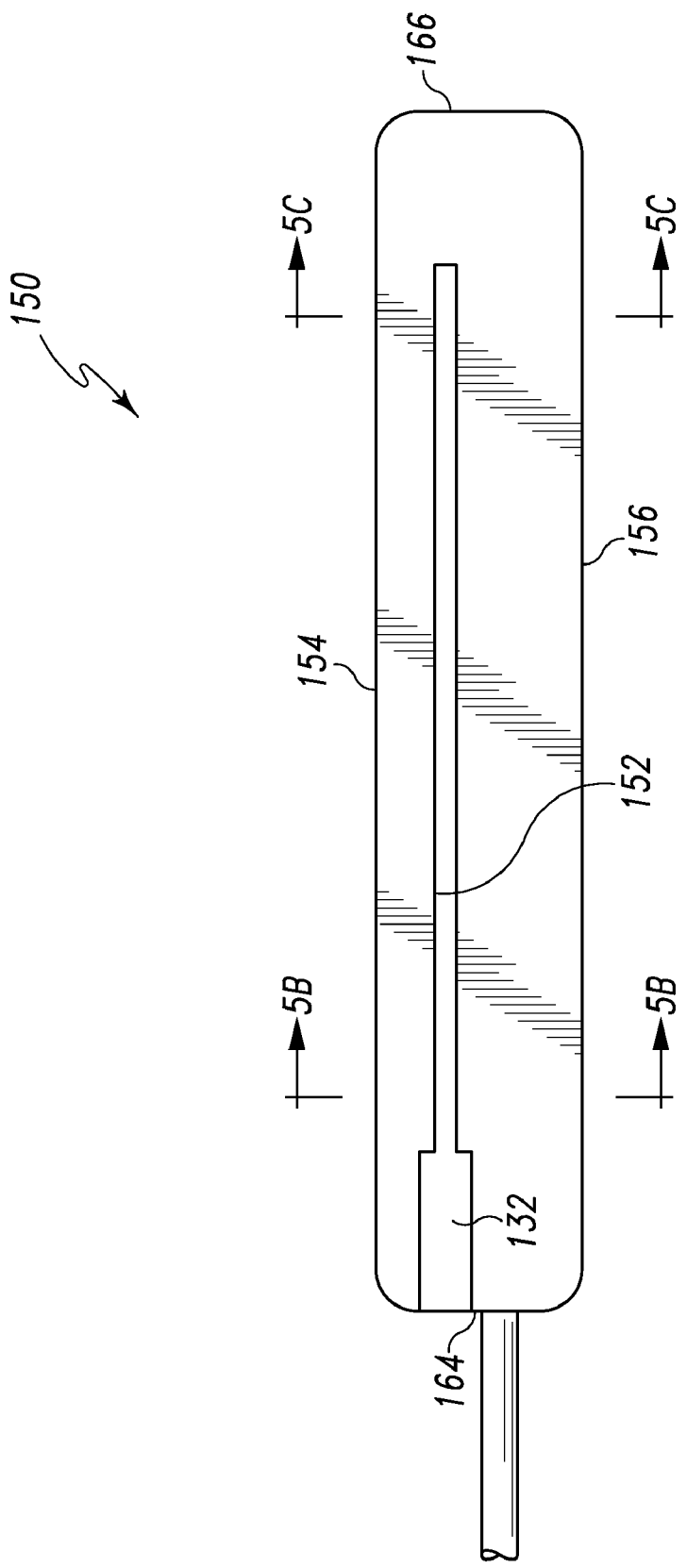
FIG. 5A is a fragmentary, top plan view of a guide according to another embodiment of the present invention.
Figure 5C:
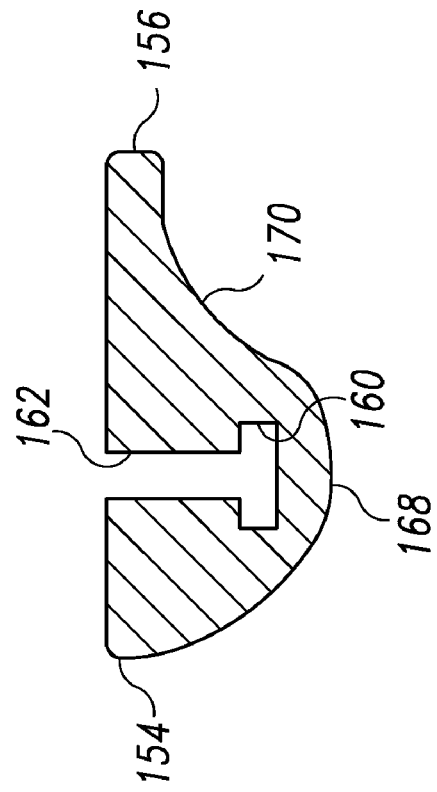
FIG. 5C is a cross-sectional view of the guide depicted in FIG. 5A taken along line 5C-5C.
Figure 5B:
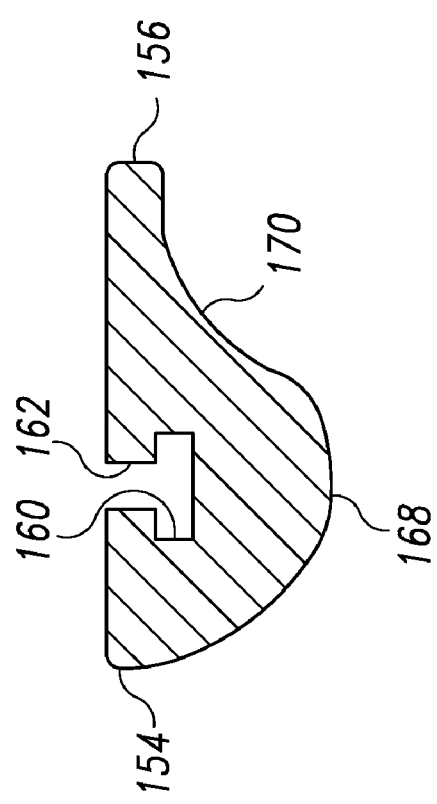
FIG. 5B is a cross-sectional view of the guide depicted in FIG. 5A taken along line 5B-5B.

Depicted in FIGS. 5A, 5B and 5C is a distal-to-proximal carpal tunnel release guide 150 according to another embodiment of the present invention. Carpal tunnel release guide 150 is adapted for surgery on the left hand and is a mirror image of the carpal tunnel release guide 100. (As with guide 100 above, the left side 154 and the right side 156 coincide with the left and right side of a surgeon holding guide 150 during surgery). Track 152 includes a wide portion 160 and a narrow portion 162 that angles downward from the guide opening end 164 to the guide terminal end 166. Furthermore, lower surface 168 includes a concave portion 170 near the right side 156 to accommodate the median nerve of the left hand when guide 150 is inserted underneath the transverse carpal ligament during surgery.

Figure 6:
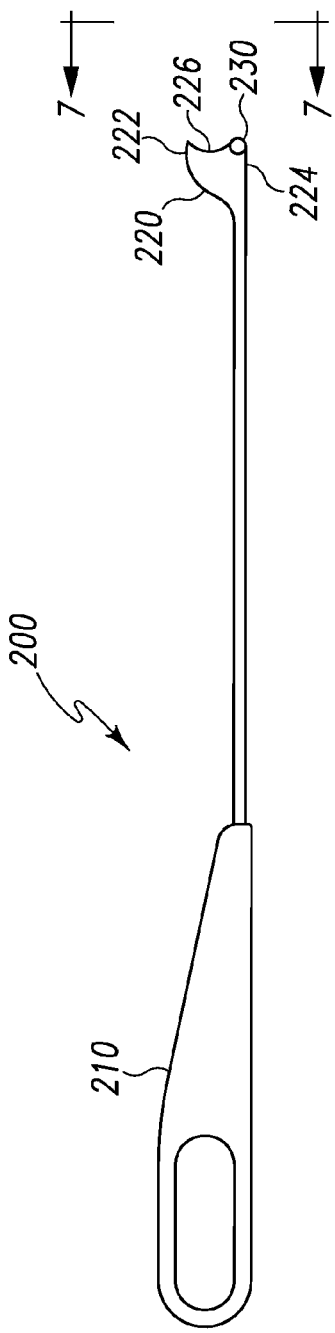
FIG. 6 is a side elevational view of a knife according to one embodiment of the present invention.
Figure 7:
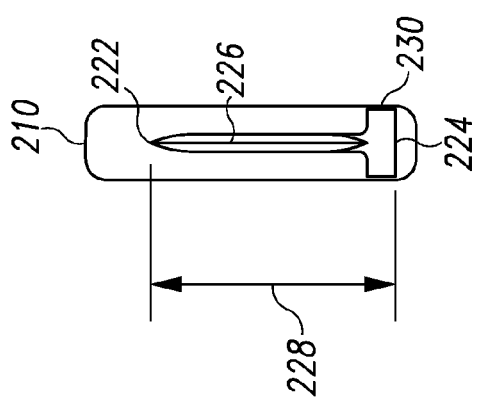
FIG. 7 is a front elevational view of the knife depicted in FIG. 6 taken from the perspective of line 7-7.

Depicted in FIGS. 6 and 7 is a carpal tunnel release tool cutting knife 200 according to one embodiment of the present invention. Cutting knife 200 includes a handle 210 and a blade 220. Blade 220 further includes an upper end 222, a lower end 224 and a cutting edge 226. Cutting knife 200 further includes a protrusion 230 located adjacent blade lower end 224.

The shape of protrusion 230 is complementary to the shape of, for example, the wide portion 140 of track 130. The width of protrusion 230 is larger than the width of track narrow portion 142 and no wider than the width of track wide portion 140. The width of blade 220 is no wider than the width of track narrow portion 142. As such, when protrusion 230 is inserted into track 130 (or track 152), blade 220 is constrained to move along track 130. For example, as blade 220 is advanced from track opening 132 to track terminal end 134 (see FIG. 3), the blade 220 is progressively retracted beneath guide upper surface 122.

The height 228 of blade 220 is approximately four and one-half millimeters (4.5 mm) when the knife 200 is used with the distal-to-proximal guides 100 and 150 (depicted in FIGS. 1-5C), and approximately five millimeters (5.0 mm) when the knife 200 is used with the proximal-to-distal guides 300 and 360 (depicted in FIGS. 12-15B). In alternate embodiments, the height 228 of blade 220 is at least three millimeters (3.0 mm) and at most nine millimeters (9.0 mm). In still further embodiments, the height 228 of blade 220 is at least three and one-half millimeters (3.5 mm) and at most six millimeters (6.0 mm).

Depicted in FIGS. 8 and 9 is a carpal tunnel release tool cutting knife 250 according to another embodiment of the present invention. Cutting knife 250 is similar to cutting knife 200 and includes a handle 251, a blade 252, a cutting edge 254 and a protrusion 256; however, cutting knife 250 further includes an upper guide 258. In use, upper guide 258 is inserted between the upper side of the transverse carpal ligament and the tissue overlying the transverse carpal ligament to further minimize damage to the tissue overlying the transverse carpal ligament.

During use, the surgeon inserts the guide 100 beneath the transverse carpal ligament through an incision in the palm of the hand and pushes the guide 100 toward the wrist/elbow, beneath the transverse carpal ligament, and above the tissue underlying the transverse carpal ligament, such as the median nerve and various connective tissue. In general, it is relatively easy for the surgeon to slide a tool underneath the transverse carpal ligament and above the underlying tissue as compared to sliding a tool above the transverse carpal ligament and below the overlying tissue. The concave portion 144 of the guide's lower surface 124 accommodates and slides along the nerve sheath of the median nerve as the nerve guide 100 is advanced under the transverse carpal ligament while the surgeon positions the upper surface 122 of guide 100 adjacent, and potentially in contact with, the transverse carpal ligament Once the guide 100 is inserted under the transverse carpal ligament, the surgeon engages cutting knife 200 with track 130 by inserting the protrusion 230 of cutting knife 200 into the wide portion 140 of track 130 with the blade 220 extending into the narrow portion 142 of track 130. See FIG. 10. The surgeon then slides the cutting knife 200 in direction D and along the T-shaped track 130 to sever the transverse carpal ligament while protecting the underlying tissue from damage from the cutting knife 200. As the cutting knife 200 slides along the T-shaped track 130, the height that the free end of cutting blade 220 extends above the upper surface 122 of the cutting guide 100 decreases—the blade 220 retracts into the cutting guide 100 and the upper end 222 of blade 220 follows the path of the wide portion 140 of track 130 as the blade 200 is advanced toward the terminal end 134 along the T-shaped track 130. As such, more of the cutting blade 220 is exposed where the transverse carpal ligament is thickest (the portion nearer the fingers) and less of the cutting blade is exposed where the transverse carpal ligament is thinnest (the portion nearer the elbow), minimizing damage to the tissue overlying the transverse carpal ligament. The free end of blade 220 which does not directly contact guide 100 (the upper end 222 in the illustrated embodiment), is restrained to follow the upper surface of ligament L as blade 220 is advanced along direction D. In alternate embodiments, the shape of track 130, and in particular the shape of the wide portion 140 of track 130, is curved to accommodate ligaments with nonlinear variations in thickness.

Figure 11:
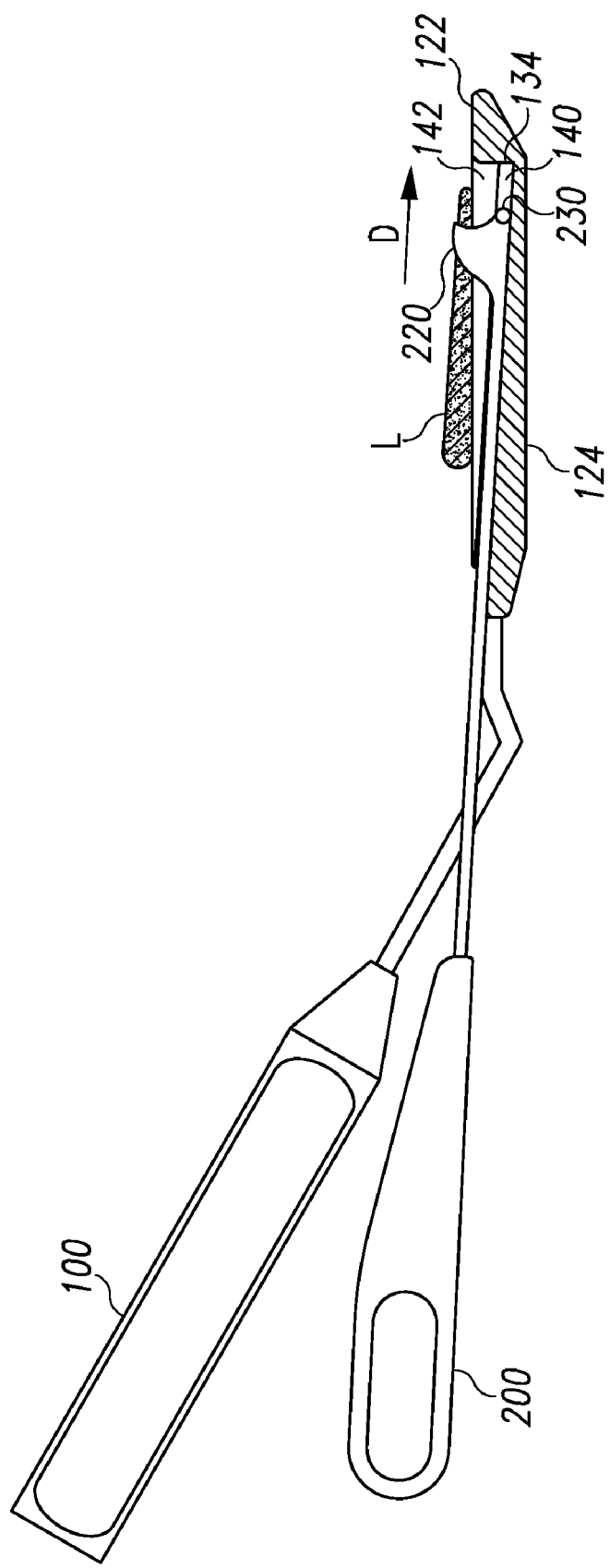
FIG. 11 is a depiction of the knife, guide and transverse carpal ligament depicted in FIG. 10 with the carpal tunnel release knife having cut through a portion of the transverse carpal ligament.

FIG. 11 depicts blade 220 as it approaches terminal end 134 of track 130 with a portion of blade 220 having been retracted beneath guide upper surface 122. In the embodiment illustrated in FIG. 11, the free end (upper end 222) of blade 220 does not fully retract below the upper surface 122 of guide 100; however, in alternate embodiments the free end (upper end 222) of blade 220 fully retracts below the upper surface 122 of guide 100. Damage to the tissue overlying the transverse carpal ligament L is minimized as the free end of blade 220 closely follows and extends only a minimal distance above the upper surface of the transverse carpal ligament L.

Figure 10:
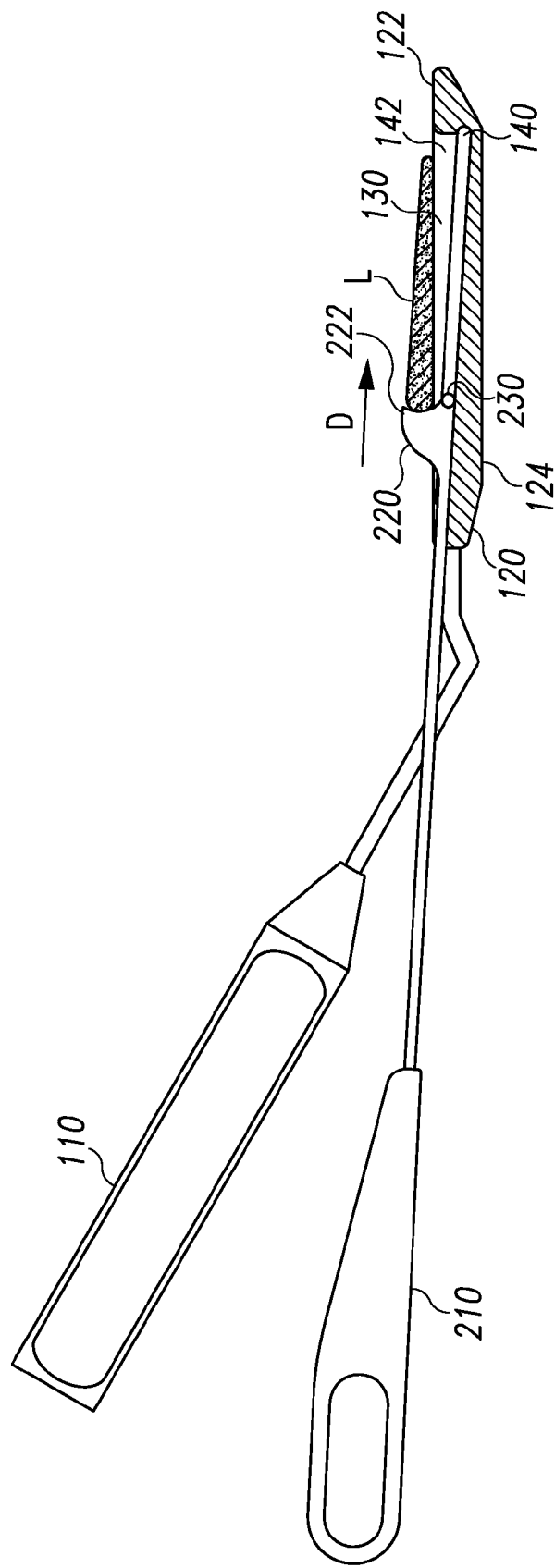
FIG. 10 is a side view of the knife depicted in FIG. 6 (depicted in side elevation) coupled with the guide depicted in FIG. 2 (depicted in cross-section along the line 10-10 in FIG. 2) and a transverse carpal tunnel ligament (depicted in cross-section along the line 10-10 in FIG. 2) according to one embodiment of the present invention.

Although FIGS. 10 and 11 depict the transverse carpal ligament as being bisected entirely by cutting knife 200, an initial pre-cut of the transverse carpal ligament may be made by the surgeon prior to insertion of guide 100 and cutting knife 200.

Depicted in FIGS. 12, 13, 14A and 14B is a proximal-to-distal carpal tunnel release guide 300 according to one embodiment of the present invention. Carpal tunnel release guide 300 is adapted for surgery on the right hand. The guide 300 is useful for insertion beneath the transverse carpal ligament in a direction opposite to the direction of the embodiments depicted in FIGS. 1-11. In other words, the proximal-to-distal guide 300 is inserted through a cut in the skin proximal to the transverse carpal ligament (near the side of the carpal tunnel ligament that is closest to the elbow) and the guide 300 is advanced toward to the distal side of the transverse carpal ligament (the side of transverse carpal ligament nearer to the fingers) before the cutting knife is inserted to bisect the transverse carpal tunnel ligament.

Guide 300 includes a handle 310 and a guide portion 320. Guide portion 320 includes an upper surface 322 spanning the distance between a right side 324 and a left side 326. (The right side 324 and the left side 326 are labeled to coincide with the right and left side of the surgeon holding guide 300 during carpal tunnel release surgery). Guide portion 320 further includes an opening end 328, which is attached to handle 310, a terminal end 329 and a projection 330 adjacent terminal end 329. Track 340 extends from the opening end 328 and into projection 330. Track 340 includes a wide portion 342, a narrow portion 344 and a blade receptacle 346. Blade receptacle encloses at least the cutting edge 154 of blade 252. Guide portion 320 further includes lower surface 348, which includes concave portion 350.

Figure 12:
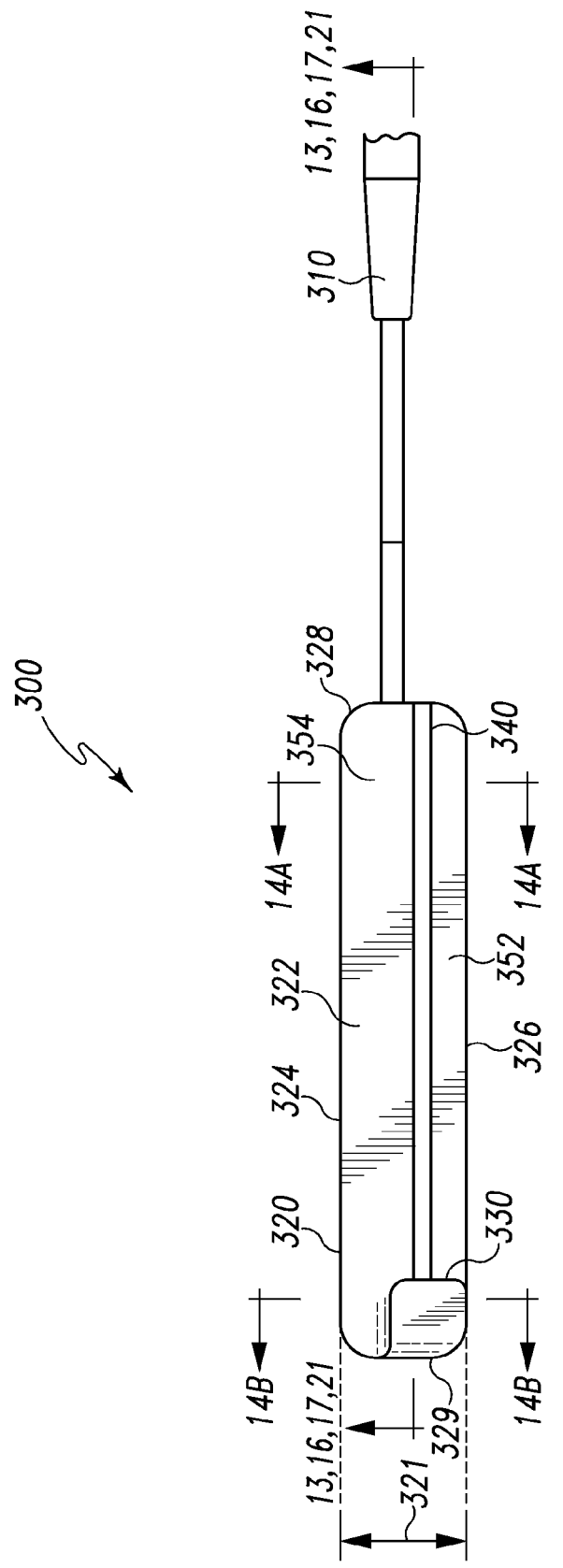
FIG. 12 is a fragmentary, top plan view of a guide according to another embodiment of the present invention.
Figure 13:
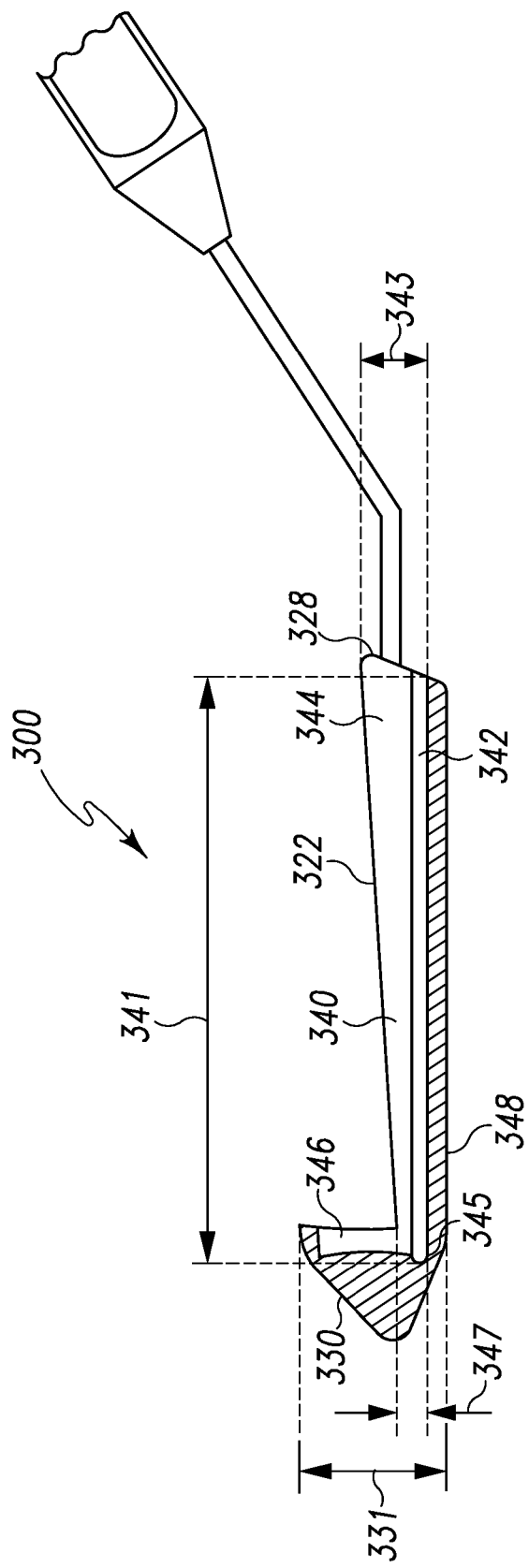
FIG. 13 is a fragmentary, cross-sectional view of the guide depicted in FIG. 12 taken along line 13-13.
Figure 14A:
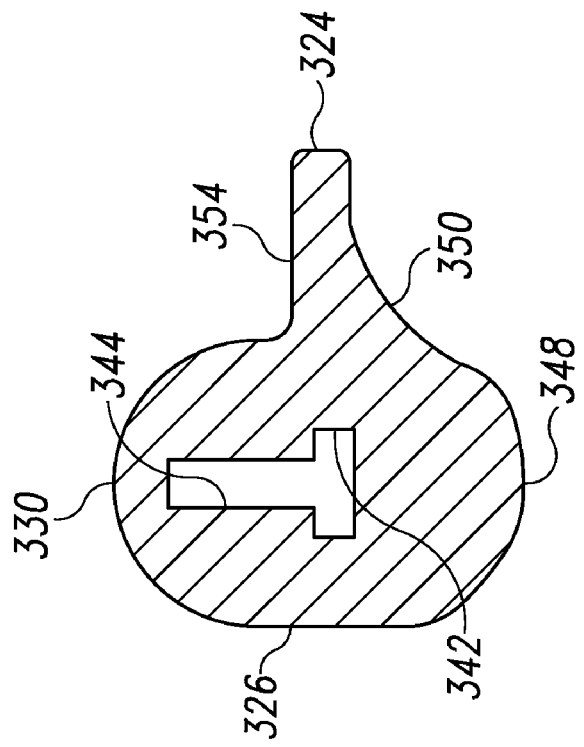
FIG. 14A is a cross-sectional view of the guide depicted in FIG. 12 taken along line 14A-14A.
Figure 14B:
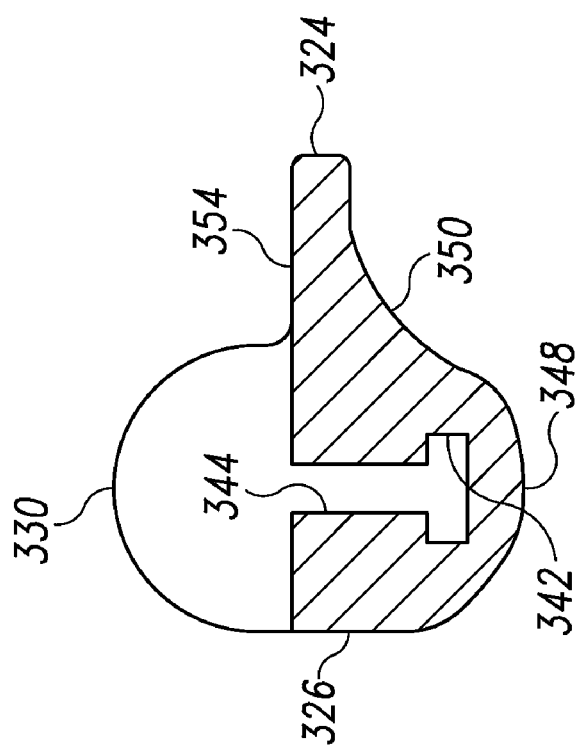
FIG. 14B is a cross-sectional view of the guide depicted in FIG. 12 taken along line 14B-14B.

As can be seen in FIG. 12, track 340 is offset nearer to left side 326 than right side 324. In the illustrated embodiment, track 340 is approximately one-third (⅓) the width 321 of guide 300 (the distance between right side 324 and left side 326) from the left side 326, and approximately two-thirds (⅔) the width 321 of guide 300 from the right side 324. As such, upper surface 322 includes a narrow side 352 adjacent left side 326 and a widened side 354 adjacent the right side 324. The concave portion 350 is located beneath the widen side 354 and accommodates the median nerve as guide 300 is inserted beneath the transverse carpal ligament. In the illustrated embodiment, the width 321 of guide 300 is nine millimeters (9 mm). In alternate embodiments, the width 321 of guide 300 is at least is at least five millimeters (5 mm) and at most thirty millimeters (30 mm). In still further embodiments, the width 321 of guide 300 is at least seven millimeters (7 mm) and at most thirteen millimeters (13 mm).

In the illustrated embodiment, the length 341 of track 340 is approximately four and three-tenths centimeters (4.3 cm). In alternate embodiments the length 431 of track 340 is at least two centimeters (2.0 cm) and at most six centimeters (6.0 cm). In still further embodiments, the length 341 of track 340 is at least three centimeters (3.0 cm) and at most five centimeters (5.0 cm).

The depth of track 340 varies along the length 341 of track 340 from the opening end 328 to the terminal end 345 of track 340. In the illustrated embodiment, the depth 343 of track 340 at the opening 328 is approximately three millimeters (3 mm) and the depth 347 of track 340 at the point where track 340 enters blade receptacle 346 is approximately one millimeter (1 mm). As such, when using a blade 220 with a five millimeter (5 mm) blade height 228 (see FIGS. 6 and 7), the upper end 222 of blade 220 extends approximately two millimeters (2 mm) above upper surface 322 at opening end 328 and extends approximately four millimeters (4 mm) above surface 322 where blade 220 enters blade receptacle 346 near track terminal end 345.

The height 331 of projection 330 is approximately 9 millimeters (9 mm) in the illustrated embodiment. The size of projection 330 should be sufficient to accommodate blade receptacle 346 and track terminal end 345 while maintaining structural integrity to avoid the forming to an extent so that the blade 220 is allowed to travel along track 340 and be received within blade receptacle 346. In alternate embodiments, the height 331 of projection 330 is at least six millimeters (6 mm) and at most twelve millimeters (12 mm).

Figure 15C:
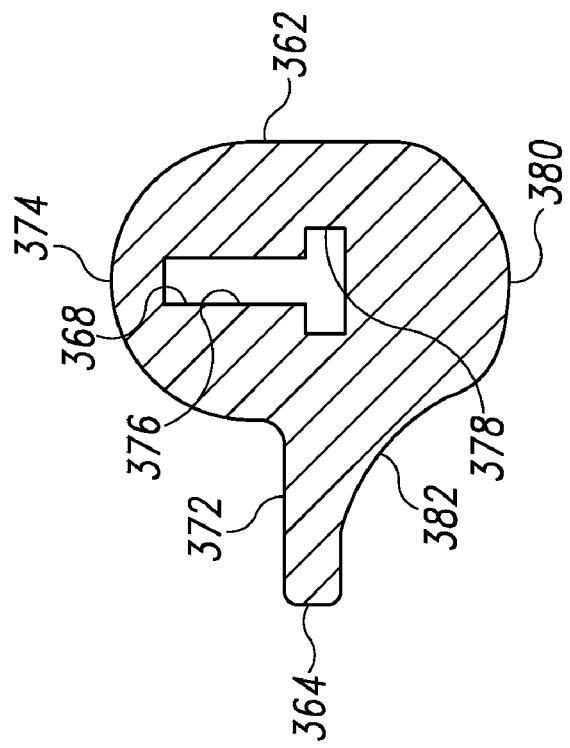
FIG. 15C is a cross-sectional view of the guide depicted in FIG. 15A taken along line 15C-15C.
Figure 15B:
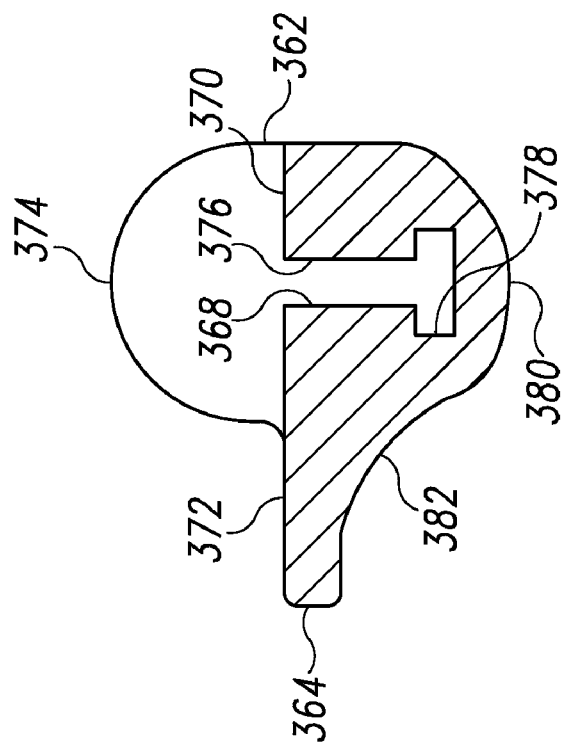
FIG. 15B is a cross-sectional view of the guide depicted in FIG. 15A taken along line 15B-15B.

Depicted in FIGS. 15A, 15B and 15C is a proximal-to-distal carpal tunnel release guide 360 for surgery according to one embodiment of the present invention. Guide 360 is adapted for surgery on a patient's left hand. Guide 360 includes a right side 362 and a left side 364, which form the boundaries of upper surface 366. A track 368 is offset to be nearer right side 362 creating a narrow portion 370 of upper surface 366 adjacent right side 362 and a widened portion 372 of upper surface 366 adjacent left side 364. The track 368 is approximately two-thirds (⅔) the width of guide 360 (the distance between left side 364 and right side 362) from left side 364, and approximately one-third the width of guide 360 from right side 362. Track 368 further includes a narrow portion 376 and a wide portion 378, and projection 374 is located at the end of track 368.

Bottom surface 380 includes a concave portion 382, which lies below the widened portion 372 and accommodates the median nerve as the carpal tunnel release guide 360 is advanced from the proximal side of the transverse carpal ligament (side nearer the elbow) to the distal side of the transverse carpal ligament (side nearer the fingers) of the left hand.

Figure 16:
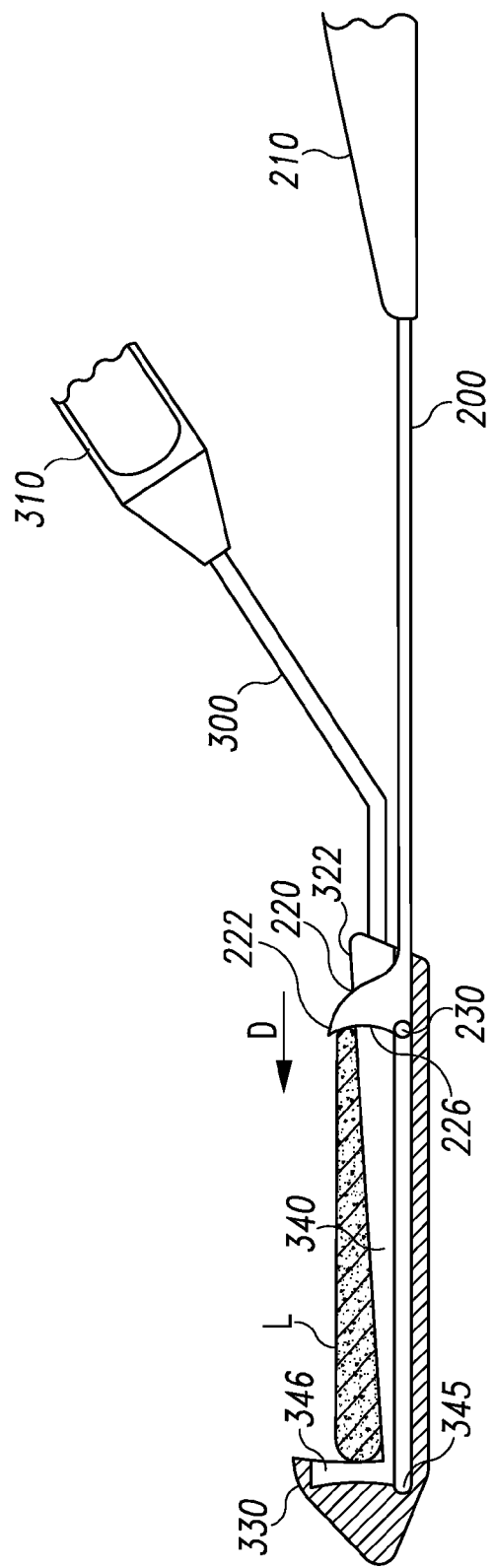
FIG. 16 is a side view of the knife depicted in FIG. 6 (depicted in side elevation) coupled with the guide depicted in FIG. 13 (depicted in cross-section along the line 16-16 in FIG. 13) and a transverse carpal tunnel ligament (depicted in cross-section along the line 16-16 in FIG. 13) according to one embodiment of the present invention.

Depicted in FIG. 16 is a cutting knife 200 inserted into the track 340 of guide 300, with guide 300 inserted beneath a transverse carpal ligament L. The width of protrusion 230 of cutting knife 200 is greater than the width of narrow portion 344 of guide 340 and at most equal to the width of wide portion 342 of track 340. The width of blade 220 is at most equal to the width of narrow portion 344 of guide 340.

When cutting knife 200 is inserted into track 340 of guide 300, the protrusion 230 of cutting knife 200 is restrained to move along the wide portion 342 of track 340. As such, the free end of blade 220 (the end portion of blade 220 not directly contacting guide 300) extends progressively further above the upper surface 322 of guide 300 as blade 220 moves toward the terminal end 345 of track 340. As such, the distance the free end (upper end 222 in the illustrated embodiment) of blade 220 extends into the tissue overlying the transverse carpal ligament L is minimized. Although depicted as following a straight line, the wide portion 342 of track 340 can be shaped to follow variously-shaped upper surfaces of transverse carpal ligament L. For example, the wide portion 342 of track 340 can be cured in part or in whole along its length.

As blade 220 approaches the terminal end 345 of track 340, the projection 330 acts as an abutment for transverse carpal ligament L restricting transverse carpal ligament L from sliding past the terminal end 345 of track 340. Projection 330 further acts as a type of cutting block and ensures that the transverse carpal ligament L is completely severed as cutting edge 226 of blade 220 is received in the blade receptacle 346 of projection 330 as the transverse carpal ligament is held outside the blade receptacle 346 by the outside surface of projection 330.

Figure 17:
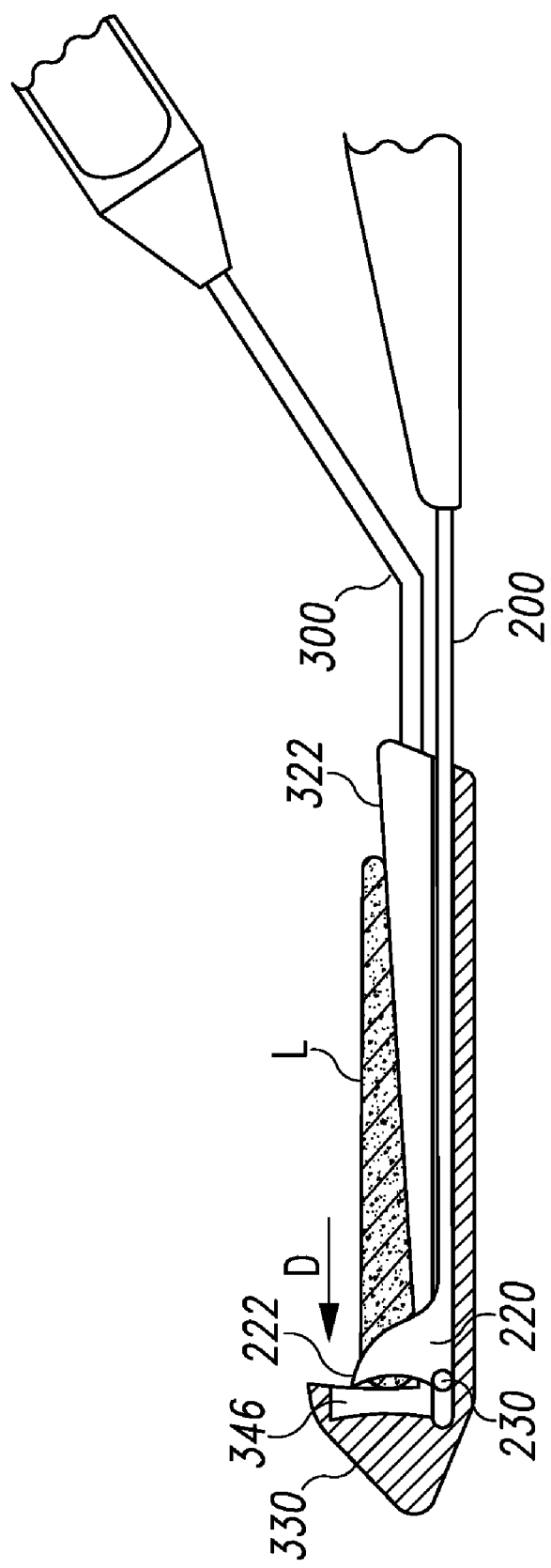
FIG. 17 is a depiction of the knife, guide and transverse carpal ligament as depicted in FIG. 16 with the carpal tunnel release knife having cut through a portion of the transverse carpal ligament.

Another feature of the projection 330 of guide 300 is to aid the surgeon in the appropriate placement of guide 300. As guide 300 is advanced beneath transverse carpal ligament L, projection 330 moves along the bottom surface of the transverse carpal ligament L. When the projection 330 advances past the far edge of the transverse carpal ligament L, the guide 300 will deflect upward and the guide will position itself with the upper surface 122 of the guide 100 adjacent to the transverse carpal ligament L as, for example, depicted in FIGS. 16 and 17. The surgeon will also be able to detect the upwardly extending position of the projection 330, giving the surgeon a positive indication that the entire transverse carpal ligament has been captured within the carpal tunnel release guide 300.

Since the thickest portion of the transverse carpal ligament is at the distal edge (nearest the fingers), the surgeon will feel a pronounced upward movement in the tip as the raised portion moves past the distal edge of the transverse carpal ligament. This feature is particularly useful when the cutting guide is inserted on the proximal side of transverse carpal ligament (side nearer the elbow) and advanced toward the distal side (side nearer the fingers) since extensive tissue damage can occur if the cutting blade extends too far past the distal edge of the transverse carpal ligament and into the palm. Although less damage generally occurs if the cutting blade extends past the proximal edge of the transverse carpal ligament in the direction of the elbow than if it extends the same distance past the distal edge of the transverse carpal ligament in the direction of the fingers, this feature can still assist surgeons in a proper positioning of the elbow guide inserted in the palm and advanced toward the elbow.

Depicted in FIGS. 18, 19 and 20 is a carpal tunnel release guide inserter 400 according to one embodiment of the present invention. Inserter 400 includes a handle 402, an upper portion 404, and a lower portion 406. Between the upper portion 404 and the lower portion 406 is a central portion 408.

Lower portion 406 and central portion 408 are sized for insertion into track 340 of guide 300. The width of lower portion 406 is at most equal to the width of the wide portion 342 of track 340, and the width of central portion 408 is at most equal to the narrow portion 344 of track 340. As such, inserter 400 may be coupled with guide 300 by inserting lower portion 406 and central portion 408 into track 340 of guide 300. The length 410 of lower portion 106 is approximately equal to the length of track 340 in guide 300. In the illustrated embodiment, the length 410 of lower portion 406 is approximately four and three-tenths centimeters (4.3 cm).

Lower portion 406 and central portion 408 are offset to one side of upper portion 404 (as best seen in FIG. 19). Additionally, the width of upper portion 404 is approximately equal to the width of the upper surface 322 of guide 300. In the depicted embodiment, the offset of lower portion 406 and central portion 408 coincides with the offset of track 340 in guide 300. As such, when inserter 400 is coupled with guide 300, the upper portion 404 of inserter 400 overlies the upper surface 322 of guide 300.

Figure 21:
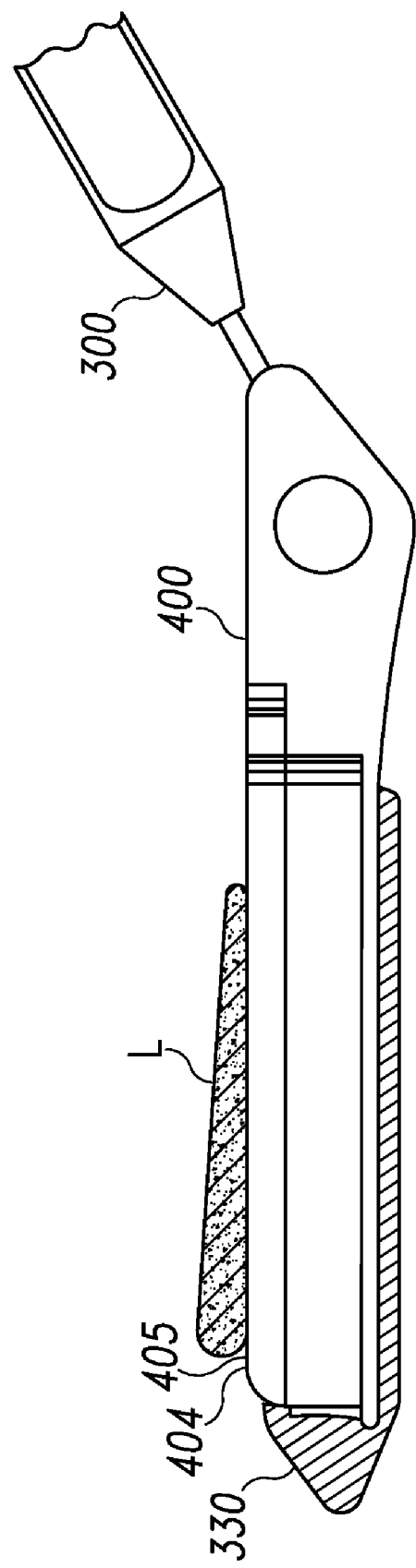
FIG. 21 is a side view of the inserter depicted in FIG. 18 (depicted in side elevation) coupled with the guide depicted in FIG. 13 (depicted in cross-section along the line 21-21 in FIG. 12) inserted beneath a transverse carpal ligament (depicted in cross-section along the line 21-21 in FIG. 12) according to one embodiment of the present invention.
Figure 22:
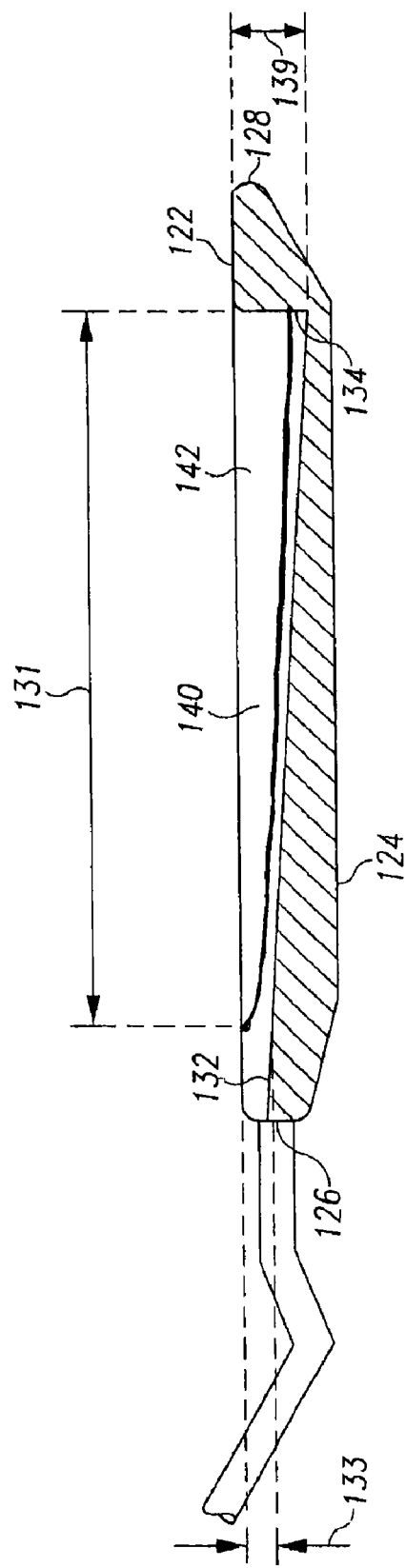
FIG. 22 is a fragmentary, cross-sectional view of an embodiment of the guide depicted in FIG. 2 taken along line 3-3 depicting the wide portion of the track defining a curved line between the track first end and the track second end.

In use, inserter 400 is coupled with guide 300 prior to the insertion of guide 300 beneath the transverse carpal ligament L. As guide 300 is advanced beneath the transverse carpal ligament L, the upper portion 404 of inserter 400 slides beneath transverse carpal ligament L and inhibits tissue from entering track 340 of guide 300. Once guide 300 is fully inserted beneath transverse carpal ligament L as depicted in FIG. 21, inserter 400 is removed and the transverse carpal ligament L is positioned adjacent the upper surface 322 of guide 300 as, for example, depicted in FIG. 16.

The surgeon may experience difficulty detecting when projection 330 extends beyond transverse carpal ligament L with the inserter 400 coupled with guide 300; however, once the inserter 400 is removed, the surgeon is able to detect whether projection 330 is properly positioned and will be able to make adjustments if necessary. In the illustrated embodiment, the upper surface 405 of upper portion 404 is positioned above the top of projection 330 when inserter 400 is coupled with guide 300. However, in alternate embodiments, the upper surface 405 of upper portion 404 is equal to the upper portion of projection 330, while in still further embodiments, the upper surface 405 of upper portion 404 is below the top of projection 330.

Although the carpal tunnel release guides 100 and 150 are described as "distal-to-proximal" guides that are inserted on the distal side of the transverse carpal ligament (in the palm of the hand) and advanced in a proximal direction (toward the elbow), beneath the transverse carpal ligament to the proximal side of the transverse carpal ligament, it should be appreciated that guides 100 and 150 are suitable for use in the opposite (proximal-to-distal) direction where they are inserted beneath the skin on the proximal side of transverse carpal ligament (nearer the elbow) and advanced in a distal direction (toward the fingers) beneath the transverse carpal ligament.

Similarly, it should be appreciated that the guides 300 and 360, while being described as "proximal-to-distal" guides that are inserted on the proximal side of the transverse carpal ligament (the side nearer the elbow) and advanced beneath the transverse carpal ligament in a distal direction (toward the fingers), the guides 300 and 360 may also be used in the opposite direction where they are inserted through an incision in the palm (on the distal side of the transverse carpal ligament) and are advanced beneath the transverse carpal ligament in a proximal direction (toward the elbow) to the proximal side of the transverse carpal ligament.

Additionally, while the disclosed carpal tunnel release tool has been described as assisting a surgeon in bisecting a transverse carpal ligament, the disclosed embodiments may be used for bisecting various types of tissue where it is desirable to have the blade either retracted or extended along a track as a blade is advanced to cut the tissue.

While illustrated examples, representative embodiments and specific forms of the invention have been illustrated and described in detail in the drawings and foregoing description, the same is to be considered as illustrative and not restrictive or limiting. The description of particular features in one embodiment does not imply that those particular features are necessarily limited to that one embodiment. Features of one embodiment may be used in combination with features of other embodiments as would be understood by one of ordinary skill in the art, whether or not explicitly described as such. Dimensions, whether used explicitly or implicitly, are not intended to be limiting and may be altered as would be understood by one of ordinary skill in the art. Only exemplary embodiments have been shown and described, and all changes and modifications that come within the spirit of the invention are desired to be protected.

What is claimed is:

1. An apparatus, comprising:
   a guide body adapted for insertion adjacent a transverse carpal ligament,
   the guide body having a planar upper surface and a length,
   the guide body defining a track having a wide portion spaced from the guide body planar upper surface and a narrow portion between the planar upper surface of the guide body and the wide portion, the track extending from a first end to a second end along the length of the guide body, the track descending from the first end to the second end, wherein the distance between the planar upper surface of the guide body and the wide portion increases along the length of the guide body from the first end to the second end; and
   a knife adapted for bisecting a transverse carpal ligament, the knife having a blade and a track engagement portion, the blade having an upper edge,
   the track engagement portion having a wide portion and a narrow portion complimentary to the wide and narrow portions of the track,
   the track engagement portion adapted for sliding engagement within the track with the blade extending outward from the guide body planar upper surface,
   the blade upper edge extending a first distance beyond the guide body planar upper surface with the blade located at the first end, and
   the blade upper edge extending a second distance beyond the guide body planar upper surface with the blade located at the second end, the second distance being less than the first distance.

2. The apparatus of claim 1, wherein the distance the blade upper edge extends beyond the guide body planar upper surface decreases as the blade advances from the track first end to the track second end.

3. The apparatus of claim 1, wherein the wide portion of the track defines a straight line between the track first end and the track second end.

4. The apparatus of claim 1, wherein the wide portion of the track defines a curved line between the track first end and the track second end.

5. The apparatus of claim 1, further comprising a guide body lower surface, wherein the guide body lower surface includes a concave portion extending along the length of the guide body.

6. The apparatus of claim 5, wherein the guide body planar upper surface has two sides defining a width, and wherein the track is positioned approximately two-thirds (⅔) the width from one of the two sides, and wherein the lower surface concave portion is adjacent said one side.

7. A system for bisecting a ligament, comprising:
   a guide for insertion near the ligament, the guide having a planar upper surface and a track, the track having a first end; and
   a blade for cutting the ligament, the blade having an engagement portion slidingly engaged with the track, the blade engagement portion being constrained to follow the track;
   wherein the blade extends beyond the planar upper surface of the guide to a free end, the free end being free from contacting the guide when the engagement portion is engaged with the first end of the track; and
   wherein the distance the blade free end extends from the planar upper surface of the guide varies as the engagement portion slides along the track from the first end.

8. The system for bisecting a ligament of claim 7, wherein the track further includes a wide portion spaced from the guide planar upper surface and a narrow portion between the guide planar upper surface and the track wide portion.

9. The system for bisecting a ligament of claim 7, wherein the track has a second end separated from the first end, and wherein the distance the blade free end extends from the planar upper surface of the guide decreases as the engagement portion slides along the track from the first end to the second end.

10. The system for bisecting a ligament of claim 7, wherein the guide has first and second sides defining a guide width, and wherein the track is positioned nearer to the first side than to the second side.

11. The system for bisecting a ligament of claim 10, wherein the guide includes a lower surface with a concave portion extending along the length of the guide, wherein the concave portion is adjacent the first side.

12. The system for bisecting a ligament of claim 7, wherein the guide has first and second sides defining a guide width, and wherein the track is positioned approximately two-thirds (⅔) of the guide width from the first side to the second side.

13. A carpal tunnel release tool, comprising:
   a blade for bisecting the transverse carpal tunnel ligament; and
   a guide body with a planar upper surface, a lower surface and a length,
   the planar upper surface forming a track with a length, the blade being slidingly engaged with the track, wherein the track includes a wide portion separated from the planar upper surface and a narrow portion between the planar upper surface and the wide portion, and wherein the distance between the guide body planar upper surface and the track wide portion varies along the track length, and
   the lower surface having a cross sectional shape perpendicular to the length, the cross sectional shape having a convex portion and one concave portion shaped to accommodate a median nerve.

14. The carpal tunnel release tool of claim 13, wherein the cross sectional shape of the lower surface is constant along the length.

15. The carpal tunnel release tool of claim 13, wherein the guide body includes a first side and a second side separated by a distance perpendicular to the track length, wherein the track and the convex portion are adjacent the first side, and wherein the concave portion is adjacent the second side.

* * * * *